(12) United States Patent
Lin et al.

(10) Patent No.: US 9,683,223 B2
(45) Date of Patent: Jun. 20, 2017

(54) AGARASE, COMPOSITION CONTAINING THE SAME, AND APPLICATION THEREOF

(71) Applicant: AGRICULTURAL TECHNOLOGY RESEARCH INSTITUTE, Hsinchu (TW)

(72) Inventors: Jiunn-Horng Lin, Hsinchu (TW);
Jyh-Perng Wang, Hsinchu (TW);
Zeng-Weng Chen, Hsinchu (TW);
Hui-Jie Lin, Hsinchu (TW);
Weng-Zeng Huang, Hsinchu (TW);
Jian-Fong Lai, Hsinchu (TW);
Shih-Ling Hsuan, Hsinchu (TW)

(73) Assignee: AGRICULTURAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 15/218,839

(22) Filed: Jul. 25, 2016

(65) Prior Publication Data

US 2017/0130217 A1    May 11, 2017

(30) Foreign Application Priority Data

Nov. 11, 2015  (TW) .............................. 104137138 A (51) Int. Cl.
  *C12N 9/24* (2006.01)
  *C12P 19/04* (2006.01)
  *C12P 19/14* (2006.01)
  *C12N 9/38* (2006.01)

(52) U.S. Cl.
  CPC ............ *C12N 9/2468* (2013.01); *C12P 19/04* (2013.01); *C12P 19/14* (2013.01); *C12Y 302/01081* (2013.01)

(58) Field of Classification Search
  None
  See application file for complete search history.

*Primary Examiner* — Suzanne M Noakes
(74) *Attorney, Agent, or Firm* — Birch, Stewart, Kolasch & Birch, LLP (57) ABSTRACT

The present invention provides a β-agarase, a composition containing the same and applications thereof. The present β-agarase provides the field a novel alternative and is favorable for the industrial utilities of the hydrolysis products of agarose. Furthermore, the hydrolysis product of agarose by the present β-agarase has high purity of neoagarotetraose therefore the present β-agarase is especially useful for the neoagarotetraose's utilities in the field.

11 Claims, 3 Drawing Sheets

AGARASE, COMPOSITION CONTAINING THE SAME, AND APPLICATION THEREOF

BACKGROUND

Technical Field

The present invention is related to an agarase, especially to an agarase produced via a prokaryotic cell expression system.

Description of Related Art

Agar is a hydrophilic polysaccharide extracted from cell walls of red algae such as *Gelidium* spp., *Gracilaria* spp., *Porphyra* spp., and etc, and the main components thereof are agarose and agaropectin. Agarose is a neutral polysaccharide with α-1,3 and β-1,4 glycosidic linkage, which is capable of forming gel and has a molecular weight of at least 100 kDa. Agaropectin is not capable of forming gel and has a molecular weight of at most 20 kDa. Agaropectin has a similar composition with agarose while some hydroxyl groups of 3,6-anhydro-α-L-galactose thereof are replaced with methoxy, sulfoxy or pyruvate groups.

Hydrolase capable of hydrolyzing agar is named agarase, which can be classified as α-agarase (EC 3.2.1.158) and β-agarase (EC 3.2.1.81) in accordance with the hydrolysis site thereof. α-Agarase hydrolyzes at the α-1,3 glycosidic linkage of agarose and agaropectin and results in agaro-oligosaccharides having 3,6-anhydro-α-L-galactose group at the reducing end thereof. β-Agarase hydrolyzes at the β-1,4 glycosidic linkage of agarose and agaropectin and results in neoagaro-oligosaccharides having D-galactose group at the reducing end thereof.

There are many applications for agarase. Case in point, agarase can be used in molecular biology research for recovery of DNA from agarose Gel, can be used in cartilage tissue engineering as agar substrate for supporting cartilage cells and thereby facilitating cartilage cells purification, increasing collagen content, and improving the culture of cartilage tissue; can be used for preparing agaro-oligosaccharide and neoagaro-oligosaccharide; can be used for preparing algae protoplast for DNA transformation and cell fusion; can be used for hydrolysis of algae polysaccharides and speculating the structure of the algae polysaccharides based on the hydrolysis product; can be used for preparing algae single cell being used as feed of marine animal breeding.

Furthermore, the current researches have proved the oligosaccharides obtained by hydrolyzing agar or algae polysaccharide crude extract exhibit several physiological and biological activities, such as antioxidation, immune regulation, antibacterial, tyrosinase suppression, moisturizing, being used as prebiotic, decreasing serum total cholesterol, and etc. The oligosaccharides can also be the new generation of high value functional oligosaccharides, which are widely applied in cosmetic, health food, and pharmaceutical industries. There are several microorganisms being proved to be able to produce agarase; nevertheless, the production of agarase by those known microorganisms encounters lost of difficulties and defects unfavorable for mass production in the industries, for instance, insufficient production, unstable production, safety concern to the bacterial used, high production cost and etc.

In light of the foregoing, the researchers in the field have considered using acid hydrolysis method to hydrolyze agar or algae polysaccharide crude extract to obtain the required oligosaccharide. However, although conventional acid hydrolysis method is able to obtain agaro-oligosaccharide mixtures, it is unable to obtain products having uniform degree of polymerization. In comparison with acid hydrolysis method, enzymatic hydrolysis has several strengths and thereby is more ideal than acid hydrolysis method. The strengths includes enzymatic selectivity in cutting specific types of glycosidic linkages to obtain oligosaccharides of desired polymerization, ease in controlling degradation condition, temperature required for enzymatic reaction is lower than that of acid hydrolysis method therefore the energy consumption is decreased, ease in operation comparing with acid hydrolysis method wherein processes like acid-base neutralization and desalination are not required, chemical agents are not necessary therefore the operation is safer and less possible in contaminating environment, and agaro-oligosaccharide and neoagaro-oligosaccharide can be obtained.

To sum up, in order to facilitate the industrial applications of the oligosaccharides obtained from agarase hydrolysis of agar or algae polysaccharide crude extract, there is a need of novel agarase to provide more options for the field. Moreover, there is also a need of a production method of agarase, which can be operated in lower cost so that the production cost of the aforesaid oligosaccharides can be decreased for facilitating commercialization.

SUMMARY

In light of the foregoing, one of the objectives of the present invention is to provide a novel agarase and thereby provide more options for the industry.

Another objective of the present invention is to provide a method for producing neoagaro-oligosaccharide by using agarase, which adopts prokaryotic cell expression systems for exogenous mass production of agarase and applies the produced agarase in hydrolysis of agar, agarose, or algae polysaccharide crude extract and reduces the product cost of neoagaro-oligosaccharide.

In order to achieve the aforesaid objectives, the present invention provides a β-agarase comprising a sequence as SEQ ID NO 01. Preferably, the β-agarase is encoded by a sequence as SEQ ID NO 02.

The present invention also provides a gene for encoding β-agarase, comprising a sequence as SEQ ID NO 02.

The present invention more provides a composition for hydrolyzing agarose, comprising: 0.1 to 10 U/mL of the β-agarase of claim 1 or claim 2; and 1 to 2 mM of a salt; wherein said U/mL and mM are based on a total volume of said composition.

Preferably, the composition further comprises 50 to 200 mM of a buffer based on a total volume of said composition; wherein said buffer is citrate buffer (pH 5 to 6) or phosphate buffer (pH 6 to 7).

Preferably, said salt is $CuSO_4$, KCl, $FeSO_4$ $BaCl_2$, NaCl, $SrCl_2$, $CoCl_2$, $MgSO_4$, $MnCl_2$, $CaCl_2$, $AlCl_3$, or a combination thereof.

Preferably, said β-agarase is produced by exogenously expressing the nucleotide sequence as SEQ ID NO 02 by a gene expression system. More preferably, said gene expression system is an *E. coli* gene expression system.

Preferably, said β-agarase is produced by exogenous expression of an expression vector contained in a gene expression system; wherein said expression vector comprises a nucleotide sequence as SEQ ID NO 02. More preferably, said expression vector has a nucleotide sequence as SEQ ID NO 05. Preferably, said exogenous expression is conducted at 15 to 32° C.

The present invention also provides a method for agarose hydrolysis, comprising the following steps: (A) providing a sample, which comprises agarose; (B) contacting said sample with said β-agarase to obtain a product.

Preferably, said product comprises 95 wt % of neoagarotetraose based on the total weight of said product.

Preferably, said product is substantially devoid of neoagarobiose and/or neoagarohexose.

Preferably, said step (B) is conducted at 40 to 45° C.

Preferably, said step (B) is conducted at pH 5 to 7.

Preferably, said step (B) for 1 to 24 hours.

Preferably, said sample is agarose, low melting point agarose, agar, algae polysaccharide crude extract, or a combination thereof.

Preferably, said β-agarase is produced by exogenously expressing the nucleotide sequence as SEQ ID NO 02 by a gene expression system.

Preferably, said gene expression system is an *E. coli* gene expression system. Preferably, said β-agarase is produced by exogenous expression of an expression vector contained in a gene expression system; wherein said expression vector comprises a nucleotide sequence as SEQ ID NO 02. More preferably, said expression vector has a nucleotide sequence as SEQ ID NO 05. Preferably, said exogenous expression is conducted at 15 to 32° C.

The present invention more provides a β-agarase expression vector, comprising: a nucleotide sequence, comprising a sequence as SEQ ID NO 02; and a regulatory element.

Preferably, said regulatory element comprises a promoter and a ribosome binding site.

Preferably, said expression vector comprises a sequence as SEQ ID NO 05.

To sum up, the present invention provides a novel agarase and teaches a method of agarose hydrolysis by using the same. It is notable that, the hydrolysis product of agarose by using the present agarase is substantially devoid of neoagarobiose and neoagarohexose. Accordingly, neoagarotetraose of high purity can be easily obtained by using the present agarase and thereby the production cost of neoagarotetraose can be favorably reduced. Moreover, the present invention provides a method for exogenously expressing agarase. The method may use an *E. coli* gene expression system to express the present agarase and thereby significantly reduces the production cost of the agarase and improves the stability in production thereof, which are both favorable for commercialization.

DETAILED DESCRIPTION

As set forth in the preceding paragraphs, although it is known to use microorganisms in producing agarase, those conventional production methods have some drawbacks. On the other hand, although prokaryotic expression systems has been used in expressing desired protein, it does not mean every kind of proteins can be produced massively by prokaryotic expression systems. There are numerous factors that could affect the production of desired protein by prokaryotic expression systems, including the distribution of the gene codon, the stability of mRNA, and stability of the desired protein, which kind of expression system is used, and the production conditions of the expression system chosen. If the desired protein is essentially not suitable for exogenous production, it would be nearly impossible to product it by a prokaryotic expression system. Furthermore, every production condition of an expression system would critically affect the capability of the expression system at issue in producing the desired protein at a commercial scale and thereby determine the production cost.

*Paenibacillus agarexedens* was first isolated from meadow soil in 1972. Before the present invention, there was no any publication reciting the agarase genes thereof. The present invention isolated a gene fragment from the bacteria and obtained a novel agarase therefrom, which may offer the industry an alternative of agarase.

In particular, one of the aspects of the present invention provides a β-agarase, which comprises a sequence as SEQ ID NO 01. Said SEQ ID NO 01 shows the amino acid sequences of the present agarase. According to the corresponding relationship between amino acid and codon, those having ordinary skill in the art shall be able to infer the nucleotide sequences encoding said SEQ ID NO 01. In a preferable embodiment, said β-agarase is translated from a sequence as SEQ ID NO 02.

Another aspect of the present invention provides a composition for hydrolyzing agarose. Said composition can be used in the industry for obtaining the hydrolysis products of agarose, such as neoagarotetraose. Said composition comprises 0.1 to 10 U/mL of said β-agarase and 1 to 2 mM of a salt; wherein said U/mL and said mM are respectively based on a total volume of said composition.

In a preferable embodiment, said salt comprises: $CuSO_4$, KCl, $FeSO_4$ $BaCl_2$, NaCl, $SrCl_2$, $CoCl_2$, $MgSO_4$, $MnCl_2$, $CaCl_2$, $AlCl_3$, or a combination thereof. Those having ordinary skill in the art shall be able to understand that said salt may exist as a metal ion and a nonmetal ion through dissociation or exist at a dissociation state and a non-dissociation state.

In a preferable embodiment, said composition may further comprise 50 to 200 mM of a buffer based on a total volume of said composition. Said buffer can be chosen as long as the chosen buffer won't affect the structure, function, or other properties of said β-agarase. For instance, said buffer could be citrate buffer (pH 5 to 6) or phosphate buffer (pH 6 to 7).

Another aspect of the present invention provides a method for agarose hydrolysis. Said method comprises the following steps: (A) providing a sample comprising agarose; (B) contacting said sample with said β-agarase and obtain a product. Said sample may be agarose, low melting point agarose, agar, algae polysaccharide crude extract, or a combination thereof.

In a preferable embodiment, said product obtained by said method comprises at least 95 weight percentage of neoagarotetraose based on a total weight of said product. In another preferable embodiment, said product is substantially devoid of neoagarobiose and neoagarohexose. Neoagarobiose, neoagarotetraose, and neoagarohexose have their industrial applications respectively; therefore, by using the present method for agarose hydrolysis, one can easily obtain a product having high purity of neoagarotetraose. In other words, there would be no need for additional purification procedure and the product can be directly used for the industry so that some production cost and time can be saved.

In a preferable embodiment, said contacting of said step (B) is conducted at a temperature of 40 to 45° C. In a preferable embodiment, said contacting of said step (B) is conducted at a pH of 5 to 7. In a preferable embodiment, said contacting of said step (B) is conducted for 1 to 24 hours.

In a preferable embodiment, said β-agarase is obtained by exogenously expressing a nucleotide sequence as SEQ ID NO 02 in a gene expression system. Said "exogenously expressing", "exogenous expression" or a like is referred to as said β-agarase is expressed in a microorganism which is not the microorganism naturally contains said β-agarase. Case in point, said β-agarase naturally exists in *P. agarexedens*. Therefore, expressing said β-agarase in an *E. coli* expression system is what the present invention defined "exogenous expression".

In a preferable embodiment, said β-agarase is obtained by an exogenous expression contacted in an *E. coli* expression system containing an expression vector. Alternatively, said expression vector comprises a nucleotide sequence as SEQ ID NO 02. In an alternative embodiment, said expression vector comprises a nucleotide sequence as SEQ ID NO 05.

As mentioned in the preceding paragraphs, every production conditions of an expression system would affect the production of the desired production and thereby affect the production cost. The efficiency of mass production of a desired protein in an expression system can be achieved by using critical production conditions. In a preferable embodiment of the present invention, a favorable temperature, 15 to 32° C., for exogenously expressing the present β-agarase in an *E. coli* expression system was proved through extensive trials and experiments in the researches of the present invention. β-agarase obtained at the aforesaid temperature range exhibits better solubility and thus is favorable for mass production for commercial need.

Another aspect of the present invention provides a β-agarase expression vector, comprising a nucleotide sequence comprising a sequence as SEQ ID NO 02; and a regulatory element. Said regulatory element is referred to as the element necessary to switch on gene transcription and translation process in an expression system. Said regulatory element shall at least comprise a promoter and a ribosome binding site. Preferably, said regulatory element may additional comprises an operator, enhancer sequences, or a combination thereof.

In a preferable, said expression vector comprises a nucleotide sequence as SEQ ID NO 05.

Experiment 1: Cloning of the Present Agarase Gene and Establishing the Present Expression Vector One open reading frame (which has an amino acid sequence as SEQ ID NO 01 having 883 amino acids; which has a nucleotide sequence as SEQ ID NO 02 having 2652 nucleotides) was chosen from the genome of *P. agarexedens* in this experiment. According to the result of protein blast analysis, the researchers of the present invention presumed that the open reading frame might encode a protein capable of hydrolyzing agarose (ie. an agarase). Before the present invention, there was never any research disclosed or hinted that the open reading frame and its potential physiological activities. Besides, the open reading frame did not share significant similarity with those known agarases in the gene sequence at the time of filing of the present invention. The present invention then established the open reading frame in an expression vector through genetic engineering for massively and stably expressing the presumed agarase in a prokaryotic gene expression system.

Strains and Culture Medium

*P. agarexedens* BCRC 17346 was purchased from Food Industry Research and Development Institute as the research subject matter of the present invention. *Escherichia coli* (ECOS 9-5, Yeastern, Taiwan) was used as the host cell for DNA cloning.

*P. agarexedens* was cultured in a nutrient broth medium (BD Difco, USA) containing 0.1% of urea and 1.5% (w/v) of agar (BD Difco, USA) can also be added for preparing solid culture plate. *E. coli* was cultured in Lurai-Bertani (LB) medium (BD Difco, USA) and antibiotic or 1.5% of agar can also be added if needed.

Extraction of Genomic DNA

A single colony of BCRC 17346 was picked and inoculated in a nutrient broth medium containing 0.1% urea and then cultured at conditions of 30° C. and 180 rpm for 24 hours. DNA purification kit (Tissue & Cell Genomic DNA Purification kit; GMbiolab, Taiwan) was used to extract the genomic DNA. First of all, 4 mL of the broth was placed in a tube and put under centrifugation (5,870×g, 5 minutes). Then, the supernatant was discarded and the pellet was collected. 200 µL of solution A (10 mM Tris-HCl, pH 8.0; 10 mM EDTA; 50 mM; NaCl; 20% (w/v) sucrose; 10 mg/mL lysozyme) was added to re-suspend the pellet. The solution A was reacted with the pellet for 1 hour at 37° C. for digesting cell wall of the bacteria. Afterward, 20 µL of proteinase K (10 mg/mL) and 200 µL of extract reagent were added in and reacted at 56° C. for 3 hours. The tube was gently shaken up side down every five minutes to let the bacterial and the reagent mix well. After that, 200 µL of binding solution was added for reaction at 70° C. for 10 minutes. Then, 200 µL of anhydrous alcohol was added and mixed in the tube and then all the contents therein was moved to a spin column. The spin column was placed in a collection tube for centrifugation. After centrifugation (17,970×g) for 2 minutes, the eluent was discarded and 300 µL of binding solution was added to the spin column and the spin column (placed in the collection tube) was centrifuged (17,970×g) for another 2 minutes. Afterward, 700 µL of wash solution was added to the spin column. After centrifugation (17,970×g) for 2 minutes, the eluent was also discarded. The washing procedure with the wash solution was repeated again. Lastly, the spin column was centrifuged (17,970×g) for another 5 minutes to remove the residual ethanol. The spin column was then placed in a clean and sterile tube and dd-water was added to elute the genomic DNA out.

Cloning of the Agarase Gene of the Present Invention

The obtained *P. agarexdens* genomic DNA was used as template for amplifying the agarase gene of the present invention by polymerase chain reaction (PCR). The PCR was conducted by using the following primer sets.

primer name: PBAGA4F
SEQ ID NO 03
GATATAGGTACCGCCACGCCGTTCCCTACTC primer name: PBAGA4R
SEQ ID NO 04
CAATATCTCGAGTTAGTGGTGGTGGTGGTGGTGCTTTGAGATT
AGCAGACGATCCATTA The 50 μL PCR mixture contained 1×GDP-HiFi PCR-bufferB, 200 μM of dNTP (dATP, dTTP, dGTP, and dCTP), 1 μM of amplification primer, 100 ng of *P. agarexdens* genomic DNA, and 1 U GDP-HiFi DNA polymerase. The PCR reaction conditions was one cycle of 98° C. for 5 minutes, 35 cycles of 94° C. for 30 seconds, 55° C. for 30 seconds, 68° C. for 90 seconds, and one cycle of 68° C. for 5 minutes.

After the PCR reaction, a gel electrophoresis was conducted to verify if a DNA fragment of expected size was obtained. Then, the PCR product was recovered by using the PCR-M™ Clean Up system kit (GeneMark, Taiwan) and by following the indication of the product manual thereof. After than the cloning of the agarase gene was conducted by using the CloneJET PCR Cloning Kit and by following the indication of the product manual thereof. The ligation mixture was transformed into *E. coli* ECOS™ 9-5. The protocol of transformation could be based on the product manual or modified according to the standard protocol known in the art.

The transformed bacteria were inoculated on LB solid plates containing ampicillin (100 μg/mL). The grown colony was picked for colony PCR for selecting strains that are transformed successfully. The PCR reaction conditions was one cycle of 95° C. for 5 minutes, 25 cycles of 95° C. for 30 seconds, 55° C. for 30 seconds, 72° C. for 3 minutes, and one cycle of 72° C. for 7 minutes. After being verified to have the desired DNA by colony PCR, the recombinant plasmid of the transformed strains was extracted for DNA sequencing (Tri-I Biotech, Inc.). The plasmid having the agarase gene of the present invention was named pJET-AGAB-4.

Establishment of the Expression Vector of the Present Invention

The plasmid pJET-AGAB-4 was cut by KpnI and XhoI. The obtained agarase gene fragment of the present invention was ligated into a plasmid pET29a cut by the same restriction enzymes by using T4 DNA ligase. The ligation product (pET29a ligated with the present agarase gene fragment) was transformed in to *E. coli* ECOS 9-5. Colony PCR was conducted for selecting transformed strains DNA gel electrophoresis was then conducted for verifying if DNA fragments of desired size exist. After being verified to have the desired insert DNA, the recombinant plasmid of the transformed strains was extracted for DNA sequencing. The plasmid having the correct sequence of the agarase gene of the present invention was named pET-AGAB-4; that is the present expression vector of SEQ ID NO 05.

Experiment 2: Establishing a Prokaryotic Expression System for Expressing the Agarase of the Present Invention Before the present invention, there had never any research successfully express of the present agarase. This experiment tried to express of present agarase in an *E. coli* expression system for the purpose of massive and stable production.

Strains and Medium

*E. coli* BL21 (DE3) was used as the hose for gene expression of this experiment. Lurai-Bertani (LB) medium (BD Difco, USA) was used for *E. coli* culture and antibiotic or 1.5% of agar can be added if needed.

The Expression of the Present Agarase at Different Temperature

The expression vector pET-AGAB-4 of the present invention was transformed into *E. coli* BL21 (DE3). A single colony was picked and inoculated in 5 mL of LB medium containing kanamycin at a final concentration of 30 μg/mL. The cells were cultured at 37° C. and 180 rpm overnight. Then, 100 μL of the broth was added in 10 mL of fresh LB medium containing kanamycin at a final concentration of 30 μg/mL and cultured at 37° C. and 180 rpm until the $OD_{600}$ value reached about 0.4 to 0.6. Afterward, 0.1 mM of isopropyl β-D-1-thiogalactopyranoside (IPTG) was added and the expression of the recombinant protein was induced at various temperatures (37° C., 30° C., 25° C., 20° C., or 16° C.). 2 mL of broth was collected at 4 and 24 hours respectively after induction. The broth was centrifuged (20,630×, 5 minutes, 4° C.) and the pellet was collected. The proteins contained in the pellet were separated based on their solubility. Protein electrophoresis was conducted to examine the solubility of the recombinant agarase.

Figure 1:
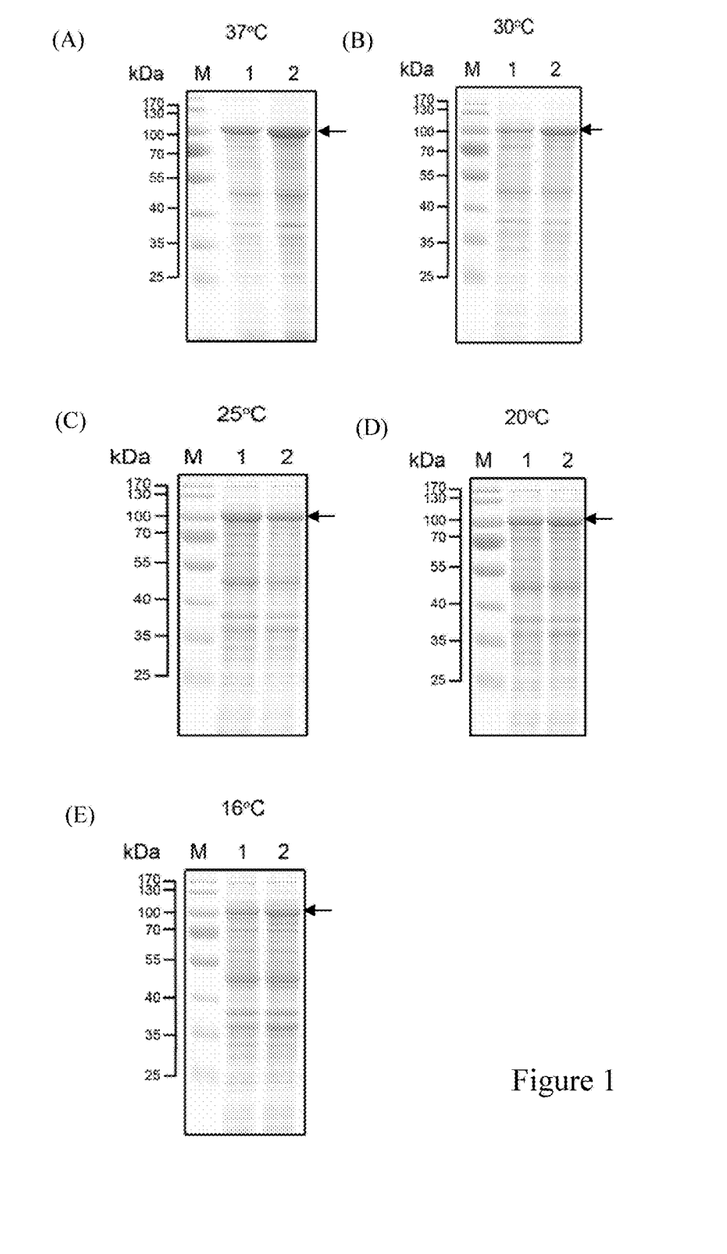
FIG. 1 is an image of protein electrophoresis. The image showed the results of Experiment 2; wherein various temperatures were used in expressing the present agarase in an *E. coli* gene expression system. (A) 37° C.; (B) 30° C.; (C) 25° C.; (D) 20° C.; (E) 16° C.; wherein the first line of each group represents the result after 4 hours expression and the second line thereof represents the result after 24 hours expression.

According to FIG. 1, it was noted that the present agarase can be successfully expressed by the *E. coli* expression system within the range of 16 to 37° C. The following Table 1 further exhibits the solubility of the present agarase expressed at different temperature. It indicated that even though the present agarase can be expressed within the range of 16 to 37° C., the yield of soluble agarase was lower when it was expressed at 37° C. In comparison, larger amount of soluble agarase can be obtained at relatively short period at 30° C., 25° C., 20° C., or 16° C. The subsequent purification process of soluble agarase is much easier than that of insoluble agarase; therefore, obtaining soluble agarase would be particular favorable for commercial scale of production.

TABLE 1

Production of soluble agarase at different induction temperature

| Induction Tem. (° C.) | Expression Time (hr) | Production of soluble agarase (mg/L) |
| --- | --- | --- |
| 37 | 4 | 1 |
|  | 24 | 4 |
| 30 | 4 | 16 |
|  | 24 | 31 |
| 25 | 4 | 32 |
|  | 24 | 37 |
| 20 | 4 | 20 |
|  | 24 | 67 |
| 16 | 4 | 16 |
|  | 24 | 52 |

Experiment 3: Analysis of the Properties of the Present Agarase

The agarase of the present invention was expressed by the expression system established in the Experiment 2 and then purified for analyzing properties thereof.

Expression and Purification of the Agarase of the Present Invention

A single colony of the *E. coli* strain (BL21/DE3, pET-AGAB-4) of Experiment 2 was picked and inoculated at 12 mL of LB medium containing kanamycin (which had a final concentration of 30 μg/mL). The culture was maintained at 37° C. and 180 rpm for overnight. Afterward, 10 mL of the broth was transferred to 1 L of fresh LB medium containing kanamycin (which had a final concentration of 30 μg/mL) and cultured at 37° C. and 180 rpm until the $OD_{600}$ value thereof achieved about 0.4 to 0.6. Then, 0.1 mM of IPTG was added at 20° C. to induce the expression of the recombinant protein. After being induced for 24 hours, pellet was collected by centrifugation (10,000×g, 10 minutes, 4° C.) and re-suspended in 10 mL of lysis buffer (20 mM sodium phosphate, 500 mM NaCl, pH 7.4). The pellet was crushed by sonicator and further centrifugation was conducted to collect the supernatant. Lastly, the supernatant was filtered by 0.22 μm filter.

Then, taking advantage of the fact that the His tag at the C-terminus of the recombinant protein can form coordinate covalent bond with nickel or cobalt ion, immobilized-metal ion affinity chromatography was used for protein purification. The purification of the recombinant agarase was conducted by using a protein liquid chromatography system, ÄKTA prime plus (GE Healthcare, Sweden) equipped with 5 mL HiTrap™ Ni excel column (GE Healthcare, Sweden). First of all, the column was balanced by 25 mL of lysis buffer and then the above-obtained supernatant was introduced into the HiTrap™ Ni excel column. After that, 100 mL of wash buffer (20 mM sodium phosphate, 500 mM NaCl, 30 mM imidazole, pH 7.4) was applied in to wash off the non-specific binding protein. Then, 150 mL of elution buffer (20 mM sodium phosphate, 500 mM NaCl, 250 mM imidazole, pH 7.4) was applied to elute the agarase binding on the resin. The theory is to compete the binding site on the resin of the recombinant protein by using high concentration of imidazole and let the recombinant agarase elute from the resin. The purified protein solution was moved to a centrifuge tube (Amicon ultra-15 ultracel-30K, Merck Millipore, USA) and stored at 4° C. after being centrifuged at 2,600×g to a proper volume.

Analysis of the Substrate of the Present Agarase

This experiment intended to test substances that can be hydrolyzed by the present agarase. 850 μL of 0.24% (w/v) agarose, low melting point agarose, agar and sodium alginate, carrageenan, soluble starch, and sodium carboxymethylcellulose solution was respectively mixed with 100 μL of 0.5 M phosphate buffer (pH 6) and heated until the contents therein was dissolved. Then, the solution was placed at 55° C. for 10 minutes. After that, 50 μL of agarase solution (being properly diluted) was added in to the substrate solution and reacted at 55° C. for 10 minutes. Afterward, 1.0 mL of DNS solution (1% 3,5-dinitrosalicylic acid, 30% potassium sodium tartrate tetrahydrate, 1.6% NaOH) was added in immediately and the mixture was heated at 100° C. for 5 minutes. After the reaction solution cooled down, 1 mL of deionized water was added in and mixed. Then, the mixture was transferred to a 96-well plate (100 μL/per well) and the absorbance at 540 nm of each well was detected by an ELISA reader. A standard curve of the reducing sugar was set by DNS color reaction of various concentrations of D-galactose solutions. The amount of the reducing sugar of each well was calculated by comparing the absorbance thereof with the D-galactose standard curve. One activity unit (U) was defined as the amount of the enzyme needed for producing 1 μmole of galactose in one minute.

Figure 2:
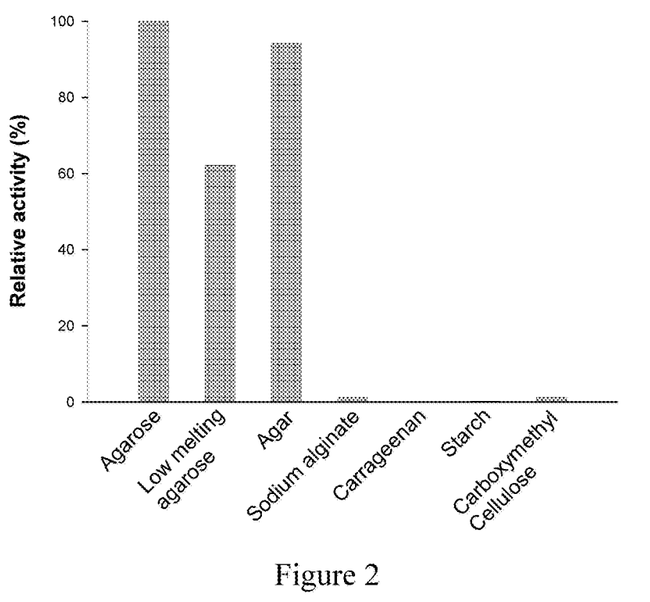
FIG. 2 shows the results of the determination to the enzymatic activity conducted in Experiment 3, showing the substrates hydrolysable by the present agarase.

The results of the experiments were shown in FIG. 2. The present agarase was able to hydrolyze agarose, low melting point agarose and agar, especially agarose. Nevertheless, the present agarase cannot hydrolyze sodium alginate, carrageenan, soluble starch, and sodium carboxymethylcellulose.

Analysis of the Hydrolysis Production of Agarose by the Present Agarase

Thin layer chromatography (TLC) was used in this experiment to analyze the hydrolysis product of agarose by the present agarase. 850 μL of 0.24% (w/v) low melting point agarose solution and 100 μL of 0.5 M phosphate buffer (pH 6) were mixed to be a mixture and heated until the contents therein were completely dissolved. Then, the mixture was placed at 40° C. for 10 minutes and then 50 μL of agarase solution (2 U/mL) was added in. The reaction was maintained at 40° C. for 24 hours. After that, the mixture was centrifuged (15,000 rpm, 4° C., 10 minutes) and filtered by 0.22 μm filter to remove bacteria therein. Then, the solution was stored at −20° C. Afterwards, 8 μL of agarase hydrolysis product, 2 μL neoagarobiose solution (10 μg/μL), 2 μL neoagarotetraose solution (10 μg/μL) and 2 μL neoagarohexose solution (10 μg/μL) were dotted on silica gel 60 TLC films (Merck Millipore, USA). After the samples dotted on the sheet were dried, the films were inserted obliquely into developing buffer (50% of 1-butanol, 25% of acetic acid, 25% of deionized water) contained in a developing tank. After developing, the TLC films were taken out for drying and then 0.1 M of aniline phthalate solution (Sigma-Aldrich, US) was sprayed over the films. After drying, the films were heated to show the color and the Rf value (retention factor value) of testing samples and standard sample was calculated. The hydrolysis product of agarase was identified through the Rf value.

Figure 3:
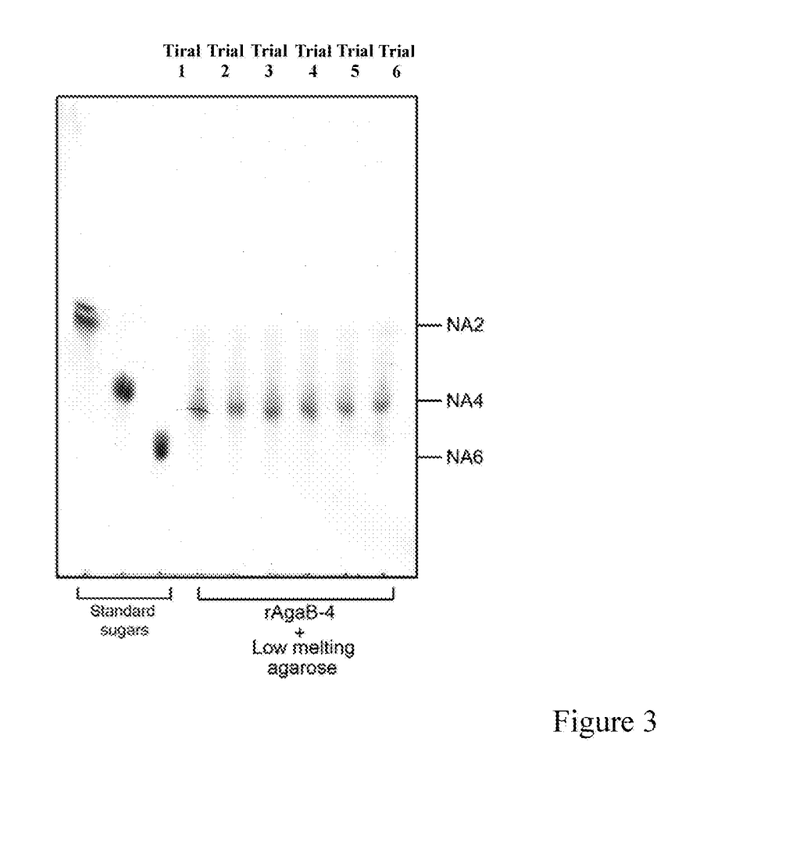
FIG. 3 shows the results of the thin layer chromatography conducted in Experiment 3, showing the hydrolysis product of low melting point agarose by the present agarase.

The results were shown in FIG. 3. According to six independent experiments, the product of hydrolyzing low melting point agarose by the present agarase was substantially neoagarotetraose and was substantially devoid of neoagarobiose and neoagarohexose. The results demonstrated that the present agarase can be used for producing neoagarotetraose of high purity and is particularly useful for the industrial application of neoagarotetraose.

Application of the Present Agarase in DNA Recovery from Gel 2.5 μg of pUC 19 plasmid and 200 μL of 1% low melting point agarose (formulated by 0.5× of TAE buffer) were mixed and placed at 4° C. for solidification. The DNA agarose gel was placed at 70° C. for 10 minutes to melt the agarose. Than, the sample was placed at 40° C. for 10 minutes. 1 U of agarase was added in and reacted at 40° C. for 1 hour. Afterwards, the mixture was centrifuged (20,630×g, 5 minutes, 4° C.) and the supernatant was collected. Then, glycogen and 10 M of ammonium acetate were added; wherein the final working concentrations thereof are respectively 1 μg/μL and 2.5 M. After that, 0.6 folds the supernatant's volume of isopropyl alcohol was added and the mixture was placed at −20° C. for 30 minutes. Then, the mixture was centrifuged at 4° C., 20,630×g for 15 minutes and the supernatant was discarded. Afterwards, 1 mL of 70% ethanol was added to re-suspend the precipitate. The suspension was then centrifuged at 4° C., 20,630×g for 10 minutes and again the supernatant was discarded. The precipitated DNA was placed at room temperature for drying and then a proper amount of sterile 10 mM Tris-HCl buffer (pH 8.0) was added to solve the DNA. Electrophoresis of 0.7% agarose gel was conducted for the recovered DNA sample and the original DNA sample (ie. pUC19 plasmid) and for calculating the recovery rate of DNA.

Figure 4:
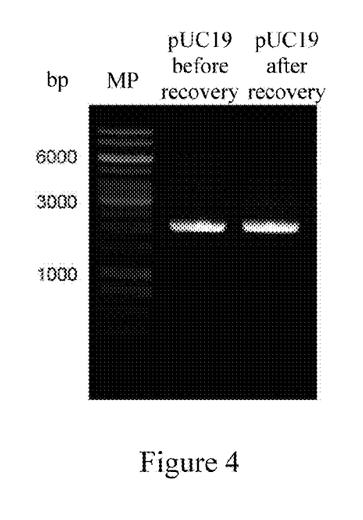
FIG. 4 shows the results of the DNA recovery assay conducted in Experiment 3, showing the efficiency of the present agarase in recovering DNA.

The results were shown in FIG. 4. The recovery rate of using the present agarase in nucleic acid sample recovery is above 95% showing that the present agarase is suitable for recovering DNA within gel.

The Effect of Metal Ions to the Activity of the Present Agarase

50 µL of 20 mM metal salt solution, 750 µL of 0.27% (w/v) agarose, and 100 µL of 0.5 M phosphate buffer (pH 6) were mixed and heated until the contents therein were completely dissolved. Then, the mixture was placed at 55° C. for 10 minutes. Afterwards, 50 µL of properly diluted agarase solution was added in to the mixture and reacted at 55° C. for 10 minutes. Subsequent DNS color reaction and enzymatic activity were conducted as set forth in the paragraphs above. Effects of different metal ions on the hydrolysis activity of the agarase of the present invention were evaluated by comparing the relative activities in each experiment group. The results were shown in the following Table 2. It exhibited that $CuSO_4$, KCl, $FeSO_4$, $BaCl_2$, NaCl, $SrCl_2$, $CoCl_2$, $MgSO_4$, $MnCl_2$, $CaCl_2$, $AlCl_3$, and etc. were able to significantly improve the activity of the present agarase.

TABLE 2

Salt and the activities of agarase

| Metal salt (metal ion) | Enzymatic activity (U) | Relative activity (%) |
|---|---|---|
| none | 0.097 | 100 |
| $CuSO_4$ ($Cu^{2+}$) | 0.110 | 113 |
| KCl ($K^+$) | 0.118 | 121 |
| $ZnSO_4$ ($Zn^{2+}$) | 0.104 | 107 |
| $FeSO_4$ ($Fe^{2+}$) | 0.109 | 112 |
| $BaCl_2$ ($Ba^{2+}$) | 0.119 | 122 |
| NaCl ($Na^+$) | 0.120 | 124 |
| $SrCl_2$ ($Sr^{2+}$) | 0.120 | 124 |
| $CoCl_2$ ($Co^{2+}$) | 0.137 | 140 |
| $MgSO_4$ ($Mg^{2+}$) | 0.112 | 116 |
| $MnCl_2$ ($Mn^{2+}$) | 0.189 | 195 |
| $CaCl_2$ ($Ca^{2+}$) | 0.118 | 121 |
| $AlCl_3$ ($Al^{3+}$) | 0.108 | 111 |

What is claimed is:

1. A method for agarose hydrolysis, comprising the following steps:
    (A) providing a sample, which comprises agarose;
    (B) contacting said sample with a composition comprising 0.1 to 10 U/ml of a β-agarase and 1-2 mM of a salt, wherein said β-agarase comprises SEQ ID NO: 1 or is encoded by SEQ ID NO: 2, wherein said U/ml and mM is based on a total volume of said composition and wherein said contacting results in a recovered hydrolyzed agarose product.

2. The method of claim 1, wherein said product comprises 95 wt % of neoagarotetraose based on the total weight of said product.

3. The method of claim 1, wherein said product is substantially devoid of neoagarobiose and/or neoagarohexose.

4. The method of claim 1, wherein said step (B) is conducted at 40 to 45° C.

5. The method of claim 1, wherein said step (B) is conducted at pH 5 to 7.

6. The method of claim 1, wherein said step (B) is conducted for 1 to 24 hours.

7. The method of claim 1, wherein said sample is agarose, low melting point agarose, agar, algae polysaccharide crude extract, or a combination thereof.

8. The method of claim 1, wherein said β-agarase is produced by exogenously expressing the nucleotide sequence as SEQ ID NO: 2 in an *E. coli* gene expression system.

9. The method of claim 1, wherein said β-agarase is produced by expression of an expression vector contained in an *E. coli* gene expression system; wherein said expression vector comprises a gene encoding said β-agarase represented by SEQ ID NO: 2.

10. The method of claim 9, wherein said expression vector comprises SEQ ID NO: 5.

11. The method of claim 9, wherein said expression is conducted at 15 to 32° C.

* * * * *

SEQUENCE LISTING

```
<160> NUMBER OF SEQ ID NOS: 5

<210> SEQ ID NO 1
<211> LENGTH: 883
<212> TYPE: PRT
<213> ORGANISM: Paenibacillus ahibensis

<400> SEQUENCE: 1

Met Ile Leu Ala Ile Ile Ala Gly Leu Thr Gly Gln Pro Gly Ala Ala
1               5                   10                  15

Ala Ala Ala Thr Pro Phe Pro Thr Leu Asn Phe Asp Asn Gly Val Ile
            20                  25                  30

Pro Ser Tyr Val Thr Gly Ser Asn Ala Thr Leu Gln Val Ile Thr Asn
        35                  40                  45

Thr Thr Gly Ser Lys Ala Leu Lys Val Asn Tyr Ala Val Ala Asp Phe
    50                  55                  60

Pro Ser Val Lys Phe Ala Pro Thr Thr Pro Trp Ser Val Gly Ser Gly
65                  70                  75                  80

Asn Ala Ile Ala Phe Glu Leu Thr Asn Ser Thr Asn Lys Asp Ile Thr
                85                  90                  95

Phe Tyr Leu Arg Val Asp Asp Ser Ala Gln Ala Asp Gly Val Lys Asp
            100                 105                 110

Ser Ile Val Ser Gln Ala Val Ala Lys Ala Gly Thr Thr Ser Gln Tyr
        115                 120                 125

Phe Leu Ser Leu Ser Ser Ala Val Leu Asp Leu Gly Met Arg Phe Leu
    130                 135                 140

Pro Pro Asn Pro Ala Gly Leu Gln Met Gly Tyr Ala Trp Gly Asp Lys
145                 150                 155                 160

Thr Val Asp Pro Ala Asn Val Val Ser Leu Gln Phe Phe Gln Met Tyr
                165                 170                 175

Pro Ser Thr Ala Thr Thr Leu Val Ile Asp Asn Leu Arg Val Ile Gln
            180                 185                 190

Asp Pro Asn Ser Asn Leu Ser Tyr Leu Asn Gly Ile Val Asp Lys Tyr
        195                 200                 205

Gly Gln Tyr Thr Val Ala Asn Trp Asn Gly Lys Val Asn Thr Asp Gln
    210                 215                 220

Asp Leu Leu Asn Asp Lys Thr Glu Glu Ala Leu Ala Leu Asn Gly Ser
225                 230                 235                 240

Gln Pro Val Ala Thr Ser Gln Tyr Gly Gly Phe Lys Asn Gly Pro Lys
```

```
            245                 250                 255
Leu Gln Ala Thr Gly Arg Phe Arg Val Ala Gln Tyr Gly Gly Lys Trp
            260                 265                 270
Thr Leu Val Asp Pro Glu Gly Tyr Leu Phe Ser Thr Gly Val Asp
            275                 280             285
Val Val Arg Leu Asp Asp Val His Thr Trp Ile Ser Gly Arg Asp Ala
            290                 295                 300
Met Phe Lys Asp Leu Pro Ala Lys Asn Ser Ser Leu Gly Glu His Phe
305                 310                 315                 320
Arg Tyr Thr Thr Thr Val Gly Ser Pro Pro Leu Gly Gln Thr Glu Gly
                    325                 330                 335
Trp Leu Phe Asn His Tyr Ser Ala Asn Leu Glu Arg Lys Tyr Gly Thr
                340                 345                 350
Asp Tyr Ile Asn Lys Trp Lys Asp Val Ser Val Ala Arg Phe Lys Asn
                355                 360                 365
Trp Gly Phe Asn Ser Leu Gly Asn Trp Ser Glu Pro Thr Leu Phe Phe
            370                 375                 380
Gly Lys Gly Ser Gln His Lys Met Ala Tyr Val Ala Asn Gly Trp Thr
385                 390                 395                 400
Ser Trp Gly Thr His Ala Thr Ile Pro Ser Gly Glu Trp Gly Gly Val
                    405                 410                 415
Ala Asp Pro Tyr Asp Pro Gln Phe Thr Val Ser Val Ser Asp Met Val
                    420                 425                 430
Gln Asn Gln Ile Leu Ala Tyr Gly Val Ala Gln Asp Pro Trp Leu Ile
                435                 440                 445
Gly Ile Tyr Val Asp Asn Glu Ile Pro Trp Gly Ser Pro Ala Thr Thr
            450                 455                 460
Gln Ser Lys Tyr Leu Leu Ile Ser Asn Ile Leu Ala Met Gln Ala Ala
465                 470                 475                 480
Asp Ser Asn Ser His Ala Lys Arg Ala Met Leu Ala His Leu Lys Thr
                    485                 490                 495
Lys Tyr Ser Asn Asn Ile Thr Leu Leu Asn Ala Gln Trp Gly Thr Ser
                500                 505                 510
Phe Ala Ser Phe Ser Ala Met Asp Ala Pro Phe Lys Pro Ala Gln Ile
            515                 520                 525
Ser Asn Gly Met Leu Pro Asp Tyr Ser Ala Met Leu Lys Leu Leu Ala
            530                 535                 540
Arg Lys Tyr Phe Ser Ile Val Asp Ala Ala Leu Thr Gln Ala Leu Pro
545                 550                 555                 560
Asn Thr Leu Tyr Leu Gly Ser Arg Phe Ala Glu Trp Gly Ile Ser Arg
                    565                 570                 575
Glu Val Gln Glu Ala Ala Glu Tyr Val Asp Val Ser Tyr Asn
                580                 585                 590
Val Tyr Lys Glu Ser Val Asn Gly His Ser Trp Met Asp Ile Ala Ala
                595                 600                 605
Leu Asn Lys Pro Ala Ile Val Gly Glu Phe Ala Phe Gly Ser Asn Asp
            610                 615                 620
Arg Gly Met Phe Gly Thr Gly Pro Asn Ser Glu Ser Ala Ala Ser Ser
625                 630                 635                 640
Gln Gln Asp Arg Ala Ala Lys Phe Thr Asn Tyr Met Asn Ala Ala Leu
                    645                 650                 655
Gln Asn Pro Tyr Phe Val Gly Ala His Trp Phe Gln Tyr Val Asp Glu
                660                 665                 670
```

```
Pro Leu Leu Gly Arg His Trp Asp Gly Glu Asn Tyr Asn Leu Gly Phe
        675                 680                 685

Val Asp Val Ala Asp Val Pro Tyr Thr Pro Leu Val Asn Ala Ala Lys
        690                 695                 700

Thr Val His Ala Gln Ala Tyr Ala Thr Arg Phe Gly Ser Thr Gly Asn
705                 710                 715                 720

Thr Lys Ile Ser Phe Glu Ala Ser Glu Asn Leu Ser Leu Ile Thr Ala
            725                 730                 735

Tyr Asn Gln Ala Thr Ile Gln Tyr Val Ser Gln Gly Ala Thr Asp Gly
        740                 745                 750

Val Arg Ala Met Lys Val Asn Val Gly Ala Leu Asp Thr Val Tyr Ala
        755                 760                 765

Gly Val Glu Val Lys Pro Ala Ser Pro Trp Asn Leu Gly Ala Ala Pro
770                 775                 780

Ser Ile Thr Ala Asp Val Thr Asn Pro Thr Ala Leu Pro Ile Gln Ile
785                 790                 795                 800

Arg Cys Asn Val Leu Asp Asn Asn Gly Gln Leu Arg Thr Phe Tyr Phe
            805                 810                 815

Thr Val Asn Ala Asn Ala Ser Arg Thr Ile Thr Met Ser Ser Phe Gly
        820                 825                 830

Ala Ser Pro Ala Gln Met Ala Gly Ala Asp Gly Tyr Trp Gly Ala Thr
        835                 840                 845

Asn Gly Leu Ser Thr Ala Gln Ile Lys Ser Ile Ser Phe Tyr Leu Trp
850                 855                 860

Glu Asp Ala Pro Gln Ser Gly Asn Ser Phe Ile Met Asp Arg Leu Leu
865                 870                 875                 880

Ile Ser Lys

<210> SEQ ID NO 2
<211> LENGTH: 2652
<212> TYPE: DNA
<213> ORGANISM: Paenibacillus ahibensis

<400> SEQUENCE: 2
atgatcttgg ctataattgc agggctgact ggacagcccg cgctgcagc tgcagccacg      60 ccgttcccta ctctaaactt cgacaatggt gtaattccct cctatgtaac cggctcgaac    120
gcgactctcc aggttattac gaacacgacg ggctccaagg cactcaaggt caattatgcg    180
gtagcagact tccatccgt gaagtttgcg ccgactacac cttggagtgt aggctccggc    240
aatgcgatcg cctttgagtt gactaattca acaaacaagg atattacgtt ctatctgcgt    300
gtggatgaca cgcccaagc cgacggcgtg aaggactcga tcgtcagtca ggcggtagcc    360
aaagccggga cgaccagcca gtactttcta agtctcagct ccgcggtgct ggacttaggt    420
atgcggttcc tgccgcccaa tcctgccggt ttgcaaatgg ttatgcctg ggggataag    480 acggtagatc ctgcgaatgt ggtttcgctg caattttttc agatgtatcc cagcacagct    540
acaaccttgg tcatcgacaa tttgagagtc atccaggacc ccaattcgaa tctaagctac    600
ttgaacggca tcgtcgataa atacggtcag tacacggtgg caaactggaa cggaaaagtg    660
aacacggatc aggatcttct gaacgacaag acggaggagg cgcttgcgct taatggctct    720
cagcccgtcg caaccagtca atacggcggc tttaagaacg gtcctaagct tcaagcaacg    780
ggacgcttca gagtcgcgca atatggaggc aagtggacct tggttgatcc tgagggggtac    840 ttattcttct cgaccggtgt ggacgttgtc cgactggatg atgtgcatac ctggatctcg    900
```

-continued

```
ggccgggacg cgatgttcaa ggatcttccg gccaagaaca gctcactcgg cgagcacttc    960
cgatatacaa cgacagtagg cagtccgccg ctggggcaaa ccgagggctg gctgttcaat   1020
cattactccg ctaacctgga acgcaaatat ggaactgatt atatcaataa atggaaggat   1080
gtatccgtag cccgcttcaa gaactggggc ttcaactcgc taggcaattg gtcggagccg   1140
acgctcttct tcggcaaggg ctcccagcac aagatggcgt atgtagccaa tggctggacc   1200
agctggggaa ctcacgctac gataccaagc ggcgagtggg gaggggttgc agatccgtac   1260
gatccgcagt tcacggtcag cgtgagcgat atggtgcaga atcaaatact agcatatggt   1320
gttgcccagg atccgtggct cattggtatt tatgtagata tgaaattcc ttggggtagc    1380 cccgccacaa cgcagagcaa atatttgttg atcagcaata ttctcgctat gcaagcagcc   1440
gatagcaaca gccatgccaa acgcgcgatg cttgctcatc tgaaaaccaa gtacagcaat   1500
aacatcacat tgctcaacgc tcagtggggc acttcattcg cctccttcag cgcgatggat   1560
gccccgttca agccggctca aatatcgaat ggcatgcttc cggactattc cgccatgctg   1620
aagcttctag cccggaagta cttcagcatt gtagatgcgg ccttaacgca agcactcccg   1680
aacactttgt atctgggctc ccgatttgcg gaatggggca ttagcagaga agtgcaggag   1740
gccgccgccg aatatgtgga tgtggtgagc tacaacgtct acaaagaatc agtgaacggc   1800
catagctgga tggatatcgc cgctcttaac aagcctgcca ttgtaggcga gtttgccttc   1860
ggttcgaatg acagaggcat gttcggcacg gggccgaatt cggaatccgc cgcgtcaagc   1920
cagcaggatc gagcagccaa atttacgaac tatatgaatg ccgccttaca aaatccgtat   1980
ttcgtaggcg cgcactggtt ccaatatgtg gatgagccgc tgctaggacg ccattgggac   2040
ggcgaaaact acaatctggg atttgtagat gtggccgacg tgccttacac gcctcttgtc   2100
aatgccgcca aaacggttca cgctcaagcc tacgccacga gattcggcag cacggggaat   2160
acgaagatat ccttcgaagc ctcggagaat ctatccctga tcaccgccta taaccaagcg   2220
actatccagt atgtgtcaca aggggcaacc gacggcgttc gtgctatgaa ggtcaatgtc   2280
ggcgctcttg atacggtata tgccggagta gaggtcaagc ccgcttcgcc gtggaattta   2340
ggagctgcgc cctccatcac ggcagatgtg accaaccta ccgcattgcc gatacagatc     2400
cgctgcaacg tgctggataa caatggacag ctgagaacgt tctattttac cgtaaatgcc   2460
aatgcttctc gcaccattac gatgagcagc ttcggcgctt cgcctgctca aatggctggg   2520
gctgacggct attggggagc aacgaatgga ttgtcgactg cccaaatcaa gtccatcagc   2580
ttctacttgt ggggaggacgc gccgcaaagc ggcaattcgt ttataatgga tcgtctgcta   2640
atctcaaagt aa                                                      2652
```

<210> SEQ ID NO 3
<211> LENGTH: 31
<212> TYPE: DNA
<213> ORGANISM: Artificial Sequence
<220> FEATURE:
<223> OTHER INFORMATION: primer

<400> SEQUENCE: 3
gatataggta ccgccacgcc gttccctact c                                    31

<210> SEQ ID NO 4
<211> LENGTH: 59
<212> TYPE: DNA
<213> ORGANISM: Artificial Sequence
<220> FEATURE:

<223> OTHER INFORMATION: primer

<400> SEQUENCE: 4

```
caatatctcg agttagtggt ggtggtggtg gtgctttgag attagcagac gatccatta    59
```

<210> SEQ ID NO 5
<211> LENGTH: 7899
<212> TYPE: DNA
<213> ORGANISM: Paenibacillus ahibensis

<400> SEQUENCE: 5

```
atccggatat agttcctcct ttcagcaaaa aacccctcaa gacccgttta gaggccccaa      60
ggggttatgc tagttattgc tcagcggtgg cagcagccaa ctcagcttcc tttcgggctt     120
tgttagcagc cggatctcag tggtggtggt ggtggtgctc gagttacttt gagattagca     180
gacgatccat tataaacgaa ttgccgcttt gcggcgcgtc ctcccacaag tagaagctga     240
tggacttgat ttgggcagtc gacaatccat tcgttgctcc ccaatagccg tcagccccag     300
ccatttgagc aggcgaagcg ccgaagctgc tcatcgtaat ggtgcgagaa gcattggcat     360
ttacggtaaa atagaacgtt ctcagctgtc cattgttatc cagcacgttg cagcggatct     420
gtatcggcaa tgcggtaggg ttggtcacat ctgccgtgat ggagggcgca gctcctaaat     480
tccacggcga agcgggcttg acctctactc cggcatatac cgtatcaaga gcgccgacat     540
tgaccttcat agcacgaacg ccgtcggttg ccccttgtga cacatactgg atagtcgctt     600
ggttataggc ggtgatcagg gatagattct ccgaggcttc gaaggatatc ttcgtattcc     660
ccgtgctgcc gaatctcgtg gcgtaggctt gagcgtgaac cgttttggcg gcattgacaa     720
gaggcgtgta aggcacgtcg gccacatcta caaatcccag attgtagttt cgccgtccc     780
aatggcgtcc tagcagcggc tcatccacat attggaacca gtgcgcgcct acgaaatacg     840
gattttgtaa ggcggcattc atatagttcg taaatttggc tgctcgatcc tgctggcttg     900
acgcggcgga ttccgaattc ggccccgtgc cgaacatgcc tctgtcattc gaaccgaagg     960
caaactcgcc tacaatggca ggcttgttaa gagcggcgat atccatccag ctatggccgt    1020
tcactgattc tttgtagacg ttgtagctca ccacatccac atattcggcg gcggcctcct    1080
gcacttctct gctaatgccc cattccgcaa atcgggagcc cagatacaaa gtgttcggga    1140
gtgcttgcgt taaggccgca tctacaatgc tgaagtactt ccgggctaga agcttcagca    1200
tggcggaata gtccggaagc atgccattcg atatttgagc cggcttgaac ggggcatcca    1260
tcgcgctgaa ggaggcgaat gaagtgcccc actgagcgtt gagcaatgtg atgttattgc    1320
tgtacttggt tttcagatga gcaagcatcg cgcgtttggc atggctgttg ctatcggctg    1380
cttgcatagc gagaatattg ctgatcaaca aatatttgct ctgcgttgtg gcggggctac    1440
cccaaggaat tcattatct acataaatac caatgagcca cggatcctgg gcaacaccat    1500
atgctagtat ttgattctgc accatatcgc tcacgctgac cgtgaactgc ggatcgtacg    1560
gatctgcaac ccctccccac tcgccgcttg gtatcgtagc gtgagttccc cagctggtcc    1620
agccattggc tacatacgcc atcttgtgct gggagccctt gccgaagaag agcgtcggct    1680
ccgaccaatt gcctagcgag ttgaagcccc agttcttgaa gcgggctacg gatacatcct    1740
tccatttatt gatataatca gttccatatt tgcgttccag gttagcggag taatgattga    1800
acagccagcc ctcggtttgc cccagcggcg gactgcctac tgtcgttgta tatcggaagt    1860
gctcgccgag tgagctgttc ttggccggaa gatccttgaa catcgcgtcc cggcccgaga    1920
tccaggtatg cacatcatcc agtcggacaa cgtccacacc ggtcgagaag aataagtacc    1980
```

```
cctcaggatc aaccaaggtc cacttgcctc catattgcgc gactctgaag cgtcccgttg   2040
cttgaagctt aggaccgttc ttaaagccgc cgtattgact ggttgcgacg ggctgagagc   2100
cattaagcgc aagcgcctcc tccgtcttgt cgttcagaag atcctgatcc gtgttcactt   2160
ttccgttcca gtttgccacc gtgtactgac cgtatttatc gacgatgccg ttcaagtagc   2220
ttagattcga attggggtcc tggatgactc tcaaattgtc gatgaccaag gttgtagctg   2280
tgctgggata catctgaaaa aattgcagcg aaaccacatt cgcaggatct accgtcttat   2340 cccccaggc ataacccatt tgcaaaccgg caggattggg cggcaggaac cgcataccta   2400
agtccagcac cgcggagctg agacttagaa agtactggct ggtcgtcccg gctttggcta   2460
ccgcctgact gacgatcgag tccttcacgc cgtcggcttg ggcgctgtca tccacacgca   2520 gataaacgt aatatccttg tttgttgaat tagtcaactc aaaggcgatc gcattgccgg   2580
agcctacact ccaaggtgta gtcggcgcaa acttcacgga tgggaagtct gctaccgcat   2640
aattgacctt gagtgccttg gagcccgtcg tgttcgtaat aacctggaga gtcgcgttcg   2700
agccggttac ataggaggga attacaccat tgtcgaagtt tagagtaggg aacggcgtgg   2760
cggtacccag atctgggctg tccatgtgct ggcgttcgaa tttagcagca gcggtttctt   2820
tcatatgtat atctccttct taaagttaaa caaaattatt tctagagggg aattgttatc   2880
cgctcacaat tccctatag tgagtcgtat taatttcgcg ggatcgagat cgatctcgat   2940
cctctacgcc ggacgcatcg tggccggcat caccggcgcc acaggtgcgg ttgctggcgc   3000
ctatatcgcc gacatcaccg atggggaaga tcgggctcgc cacttcgggc tcatgagcgc   3060
ttgtttcggc gtgggtatgg tggcaggccc cgtggccggg ggactgttgg cgccatctc    3120 cttgcatgca ccattccttg cggcggcggt gctcaacggc ctcaacctac tactgggctg   3180
cttcctaatg caggagtcgc ataagggaga gcgtcgagat cccggacacc atcgaatggc   3240
gcaaaacctt tcgcggtatg gcatgatagc gcccggaaga gagtcaattc agggtggtga   3300
atgtgaaacc agtaacgtta tacgatgtcg cagagtatgc cggtgtctct tatcagaccg   3360
tttcccgcgt ggtgaaccag gccagccacg tttctgcgaa aacgcgggaa aaagtggaag   3420
cggcgatggc ggagctgaat tacattccca accgcgtggc acaacaactg gcgggcaaac   3480
agtcgttgct gattggcgtt gccacctcca gtctggccct gcacgcgccg tcgcaaattg   3540
tcgcggcgat taaatctcgc gccgatcaac tgggtgccag cgtggtggtg tcgatggtag   3600
aacgaagcgg cgtcgaagcc tgtaaagcgg cggtgcacaa tcttctcgcg caacgcgtca   3660
gtgggctgat cattaactat ccgctggatg accaggatgc cattgctgtg gaagctgcct   3720
gcactaatgt tccggcgtta tttcttgatg tctctgacca gacacccatc aacagtatta   3780
ttttctccca tgaagacggt acgcgactgg gcgtggagca tctggtcgca ttgggtcacc   3840
agcaaatcgc gctgttagcg ggcccattaa gttctgtctc ggcgcgtctg cgtctggctg   3900
gctggcataa atatctcact cgcaatcaaa ttcagccgat agcggaacgg gaaggcgact   3960
ggagtgccat gtccggtttt caacaaacca tgcaaatgct gaatgagggc atcgttccca   4020
ctgcgatgct ggttgccaac gatcagatgg cgctgggcgc aatgcgcgcc attaccgagt   4080
ccgggctgcg cgttggtgcg gacatctcgg tagtgggata cgacgatacc gaagacagct   4140
catgttatat cccgccgtta accaccatca aacaggattt tcgcctgctg gggcaaacca   4200
gcgtggaccg cttgctgcaa ctctctcagg ccaggcggt gaagggcaat cagctgttgc   4260
ccgtctcact ggtgaaaaga aaaaccaccc tggcgcccaa tacgcaaacc gcctctcccc   4320
```

```
gcgcgttggc cgattcatta atgcagctgg cacgacaggt ttcccgactg gaaagcgggc    4380
agtgagcgca acgcaattaa tgtaagttag ctcactcatt aggcaccggg atctcgaccg    4440
atgcccttga gagccttcaa cccagtcagc tccttccggt gggcgcgggg catgactatc    4500
gtcgccgcac ttatgactgt cttctttatc atgcaactcg taggacaggt gccggcagcg    4560
ctctgggtca ttttcggcga ggaccgcttt cgctggagcg cgacgatgat cggcctgtcg    4620
cttgcggtat tcggaatctt gcacgccctc gctcaagcct tcgtcactgg tcccgccacc    4680
aaacgtttcg gcgagaagca ggccattatc gccggcatgg cggcccacg ggtgcgcatg    4740 atcgtgctcc tgtcgttgag gacccggcta ggctggcggg gttgccttac tggttagcag    4800
aatgaatcac cgatacgcga gcgaacgtga agcgactgct gctgcaaaac gtctgcgacc    4860
tgagcaacaa catgaatggt cttcggtttc cgtgtttcgt aaagtctgga acgcggaag    4920 tcagcgccct gcaccattat gttccggatc tgcatcgcag gatgctgctg gctaccctgt    4980
ggaacaccta catctgtatt aacgaagcgc tggcattgac cctgagtgat ttttctctgg    5040
tcccgccgca tccataccgc cagttgttta ccctcacaac gttccagtaa ccgggcatgt    5100
tcatcatcag taacccgtat cgtgagcatc ctctctcgtt tcatcggtat cattacccccc    5160 atgaacagaa atccccctta cacggaggca tcagtgacca aacaggaaaa aaccgccctt    5220
aacatggccc gctttatcag aagccagaca ttaacgcttc tggagaaact caacgagctg    5280
gacgcggatg aacaggcaga catctgtgaa tcgcttcacg accacgctga tgagctttac    5340
cgcagctgcc tcgcgcgttt cggtgatgac ggtgaaaacc tctgacacat gcagctcccg    5400
gagacggtca cagcttgtct gtaagcggat gccgggagca gacaagcccg tcagggcgcg    5460
tcagcgggtg ttggcgggtg tcggggcgca gccatgaccc agtcacgtag cgatagcgga    5520
gtgtatactg gcttaactat gcggcatcag agcagattgt actgagagtg caccatatat    5580
gcggtgtgaa ataccgcaca gatgcgtaag gagaaaatac cgcatcaggc gctcttccgc    5640
ttcctcgctc actgactcgc tgcgctcggt cgttcggctg cggcgagcgg tatcagctca    5700
ctcaaaggcg gtaatacggt tatccacaga atcagggat aacgcaggaa agaacatgtg    5760
agcaaaaggc cagcaaaagg ccaggaaccg taaaaaggcc gcgttgctgg cgttttcca    5820 taggctccgc cccctgacg agcatcacaa aaatcgacgc tcaagtcaga ggtggcgaaa    5880
cccgacagga ctataaagat accaggcgtt tccccctgga agctccctcg tgcgctctcc    5940
tgttccgacc ctgccgctta ccggatacct gtccgccttt ctcccttcgg gaagcgtggc    6000
gctttctcat agctcacgct gtaggtatct cagttcggtg taggtcgttc gctccaagct    6060
gggctgtgtg cacgaacccc ccgttcagcc cgaccgctgc gccttatccg gtaactatcg    6120
tcttgagtcc aacccggtaa gacacgactt atcgccactg gcagcagcca ctggtaacag    6180
gattagcaga gcgaggtatg taggcggtgc tacagagttc ttgaagtggt ggcctaacta    6240
cggctacact agaaggacag tatttggtat ctgcgctctg ctgaagccag ttaccttcgg    6300
aaaaagagtt ggtagctctt gatccggcaa acaaaccacc gctggtagcg gtggtttttt    6360
tgtttgcaag cagcagatta cgcgcagaaa aaaaggatct caagaagatc ctttgatctt    6420
ttctacgggg tctgacgctc agtggaacga aaactcacgt taagggattt tggtcatgaa    6480
caataaaact gtctgcttac ataaacagta atacaagggg tgttatgagc catattcaac    6540
gggaaacgtc ttgctctagg ccgcgattaa attccaacat ggatgctgat ttatatgggt    6600
ataaatgggc tcgcgataat gtcgggcaat caggtgcgac aatctatcga ttgtatggga    6660
agcccgatgc gccagagttg tttctgaaac atggcaaagg tagcgttgcc aatgatgtta    6720
```

```
cagatgagat ggtcagacta aactggctga cggaatttat gcctcttccg accatcaagc      6780
attttatccg tactcctgat gatgcatggt tactcaccac tgcgatcccc gggaaaacag      6840
cattccaggt attagaagaa tatcctgatt caggtgaaaa tattgttgat gcgctggcag      6900
tgttcctgcg ccggttgcat tcgattcctg tttgtaattg tccttttaac agcgatcgcg      6960
tatttcgtct cgctcaggcg caatcacgaa tgaataacgg tttggttgat gcgagtgatt      7020
ttgatgacga gcgtaatggc tggcctgttg aacaagtctg gaaagaaatg cataaacttt      7080
tgccattctc accggattca gtcgtcactc atggtgattt ctcacttgat aaccttattt      7140
ttgacgaggg gaaattaata ggttgtattg atgttggacg agtcggaatc gcagaccgat      7200
accaggatct tgccatccta tggaactgcc tcggtgagtt ttctccttca ttacagaaac      7260 ggcttttca aaaatatggt attgataatc ctgatatgaa taaattgcag tttcatttga      7320
tgctcgatga gttttctaa gaattaattc atgagcggat acatatttga atgtatttag       7380
aaaaataaac aaatagggt tccgcgcaca tttccccgaa aagtgccacc tgaaattgta       7440
aacgttaata ttttgttaaa attcgcgtta aattttgtt aaatcagctc attttttaac       7500
caataggccg aaatcggcaa aatcccttat aaatcaaaag aatagaccga gatagggttg      7560
agtgttgttc cagtttggaa caagagtcca ctattaaaga acgtggactc caacgtcaaa      7620
gggcgaaaaa ccgtctatca gggcgatggc ccactacgtg aaccatcacc ctaatcaagt      7680
tttttggggt cgaggtgccg taaagcacta aatcggaacc ctaaagggag cccccgattt      7740
agagcttgac ggggaaagcc ggcgaacgtg gcgagaaagg aagggaagaa agcgaaagga      7800
gcgggcgcta gggcgctggc aagtgtagcg gtcacgctgc gcgtaaccac cacacccgcc      7860
gcgcttaatg cgccgctaca gggcgcgtcc cattcgcca                            7899
```